United States Patent
Kawata et al.

(10) Patent No.: US 9,207,211 B2
(45) Date of Patent: Dec. 8, 2015

(54) DEPOSIT MEASUREMENT APPARATUS, DEPOSIT MEASUREMENT METHOD, AND COMPUTER-READABLE STORAGE MEDIUM STORING DEPOSIT MEASUREMENT PROGRAM

(75) Inventors: Kayoko Kawata, Tokyo (JP); Yuko Yamamoto, Tokyo (JP); Masaaki Kurokawa, Tokyo (JP); Masaharu Michihashi, Tokyo (JP); Naoto Kawase, Tokyo (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 943 days.

(21) Appl. No.: 13/293,766

(22) Filed: Nov. 10, 2011

(65) Prior Publication Data

US 2012/0179402 A1 Jul. 12, 2012

(30) Foreign Application Priority Data

Jan. 6, 2011 (JP) ................... 2011-001269

(51) Int. Cl.
| | |
|---|---|
| *G01B 7/02* | (2006.01) |
| *G01N 27/90* | (2006.01) |
| *G01N 17/00* | (2006.01) |
| *G01B 7/06* | (2006.01) |
| *F22B 37/00* | (2006.01) |

(52) U.S. Cl.
CPC .......... *G01N 27/9046* (2013.01); *F22B 37/003* (2013.01); *G01B 7/105* (2013.01); *G01N 17/008* (2013.01); *G01N 27/90* (2013.01)

(58) Field of Classification Search
USPC .......................................................... 702/65
See application file for complete search history.

(56) References Cited

U.S. PATENT DOCUMENTS

| | | | | |
|---|---|---|---|---|
| 4,188,577 | A | * | 2/1980 | Mhatre et al. ................ 324/220 |
| 4,247,819 | A | * | 1/1981 | Shimada et al. ............ 324/233 |
| 5,408,883 | A | * | 4/1995 | Clark et al. ..................... 73/601 |
| 6,308,774 | B1 | * | 10/2001 | Kramer et al. ................. 165/95 |
| 6,366,083 | B1 | | 4/2002 | McClelland |

(Continued)

FOREIGN PATENT DOCUMENTS

| | | |
|---|---|---|
| FR | 2 834 341 A1 | 7/2003 |
| FR | 2 928 024 A1 | 8/2009 |

(Continued)

OTHER PUBLICATIONS

Extended European Search Report dated Apr. 2, 2012, issued in European Patent Application No. 11191389.3, (14 pages).

(Continued)

*Primary Examiner* — Paul D Lee

(74) *Attorney, Agent, or Firm* — Westerman, Hattori, Daniels & Adrian, LLP

(57) ABSTRACT

An object is to improve the precision of estimating a blockage ratio or a deposited-scale thickness. In a deposit measurement apparatus that estimates a blockage ratio of a gap between a wall surface of a through-hole and an outer surface of a heat-conducting pipe or the thickness of a deposit deposited at the gap, an eddy-current flaw detection probe (61) acquires an eddy-current flaw detection signal by scanning inside the heat-conducting pipe with a sensor; and a processing device (62) estimates the blockage ratio at the gap or the thickness of the deposit deposited at the gap by using the eddy-current flaw detection signal for the gap of the pipe-supporting-plate protrusion in the through-hole.

18 Claims, 11 Drawing Sheets

(56) References Cited

U.S. PATENT DOCUMENTS

| | | |
|---|---|---|
| 2009/0223053 A1* | 9/2009 | Gandy et al. ............. 29/890.031 |
| 2011/0022333 A1 | 1/2011 | Griffith et al. |
| 2011/0241660 A1 | 10/2011 | Gemma |
| 2012/0002775 A1 | 1/2012 | Debroise et al. |
| 2012/0330474 A1* | 12/2012 | Kreider et al. ................ 700/292 |
| 2013/0335551 A1* | 12/2013 | Mandier et al. ................ 348/84 |

FOREIGN PATENT DOCUMENTS

| | | |
|---|---|---|
| FR | 2 960 336 A1 | 11/2011 |
| GB | 2 055 473 A | 3/1981 |
| JP | 56-6178 A | 1/1981 |
| JP | 64-50953 A | 2/1989 |
| JP | 5-87510 A | 4/1993 |
| JP | 06-011332 A | 1/1994 |
| JP | 8-233510 A | 9/1996 |
| JP | 11-307567 A | 11/1999 |
| JP | 2001-133208 A | 5/2001 |
| JP | 2002-181793 A | 6/2002 |
| JP | 2002-195984 A | 7/2002 |
| JP | 2003-075409 A | 3/2003 |
| JP | 2003-279287 A | 10/2003 |
| JP | 2005-164457 A | 6/2005 |
| JP | 2005-286309 A | 10/2005 |
| JP | 2006-118800 A | 5/2006 |
| JP | 2007-178380 A | 7/2007 |
| JP | 2009-168475 A | 7/2009 |
| JP | 2009-192410 A | 8/2009 |
| JP | 2009543094 A | 12/2009 |
| JP | 2010-127665 A | 6/2010 |
| JP | 2012-504756 A | 2/2012 |
| WO | 2008/100267 A2 | 8/2008 |
| WO | 2010/037869 A1 | 4/2010 |

OTHER PUBLICATIONS

Japanese Office Action dated Dec. 24, 2013, issued in Japanese Patent Application No. 2011-001269, w/English translation, (16 pages).

European Search Report dated Apr. 2, 2012, issued in corresponding European Patent Application No. 11191389.3, (14 pages).

Châtellier, et al., "Tube Support Plate Blockage Evaluation With Televisual Examination and Eddy Current Analysis", AIP Conference Proceedings, dated Jan. 1, 2009 pp. 766-773, XP55022381, cited in European Search Report dated Apr. 2, 2012.

Paillard, et al., "Simulation of Eddy Current Testing of Steam Generator Tubes in the Proximity of Support Plates Quadrefoil-Shaped Holes With an Hybrid Finite Fe-Vim Model", Proceedings of the European Conference on Non-Destructive Testing, dated Jun. 11, 2010, pp. 1-8, XP55022400. Conference Cited in European Search Report dated Apr. 2, 2012.

Bodineau, et al., "Tube Support Plate Clogging Up of French PWR Steam Generators", Eurosafe—Towards Convergence of Technical Nuclear Safety in Europe, dated Nov. 3, 2008, pp. 1-9, XP55022336. Cited in European Search Report dated Apr. 2, 2012.

Japanese Office Action dated Sep. 9, 2014, issued in Japanese Patent Application No. 2011-001269, w/English translation (7 pages).

Japanese Office Action dated Feb. 24, 2015, issued in corresponding JP Patent Application No. 2011-001269 with English translation (12 pages).

Decision to Grant Patent dated Jul. 7, 2015, issued in counterpart Japanese application No. 2011-001269, w/ English translation (8 pages).

* cited by examiner

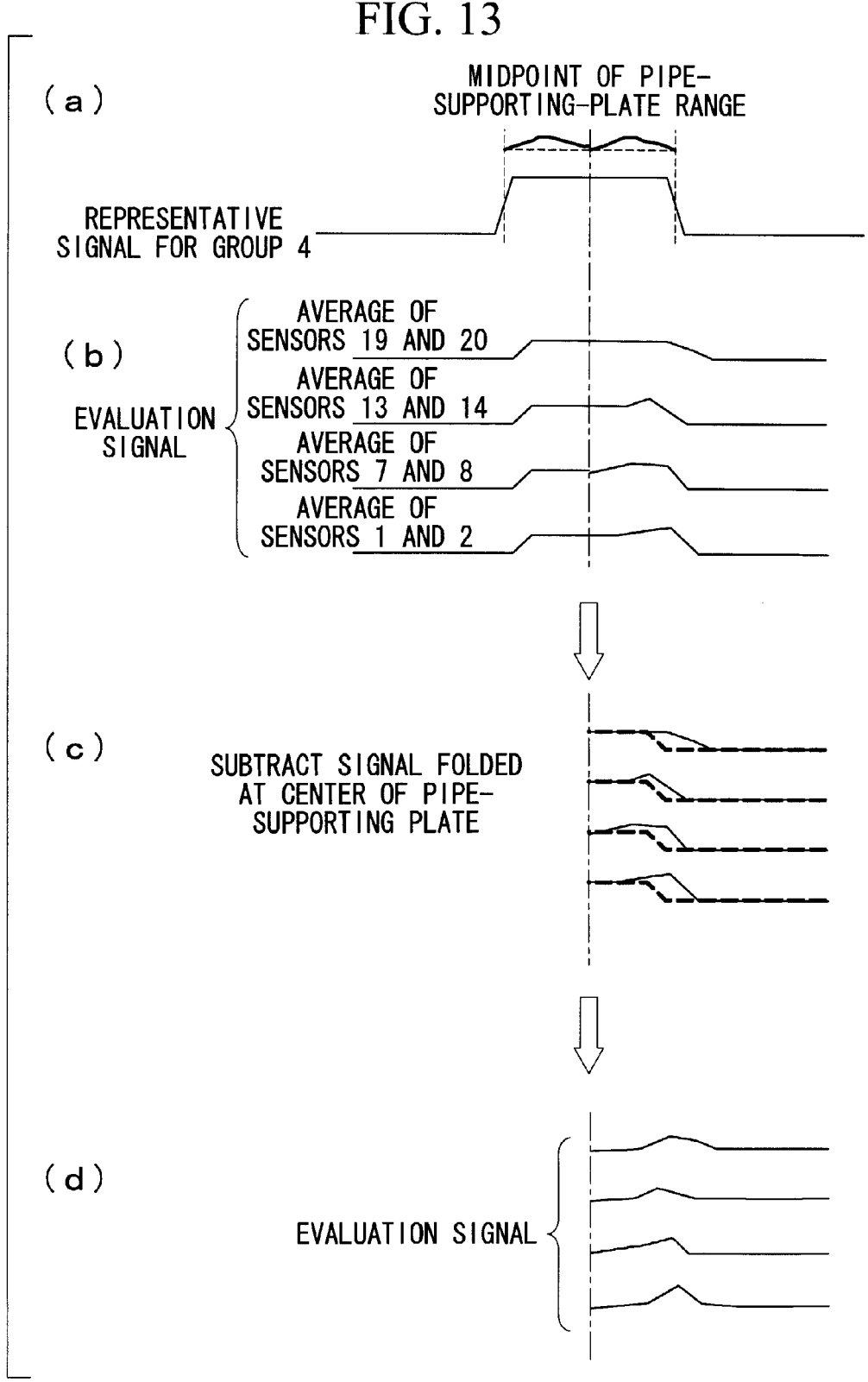

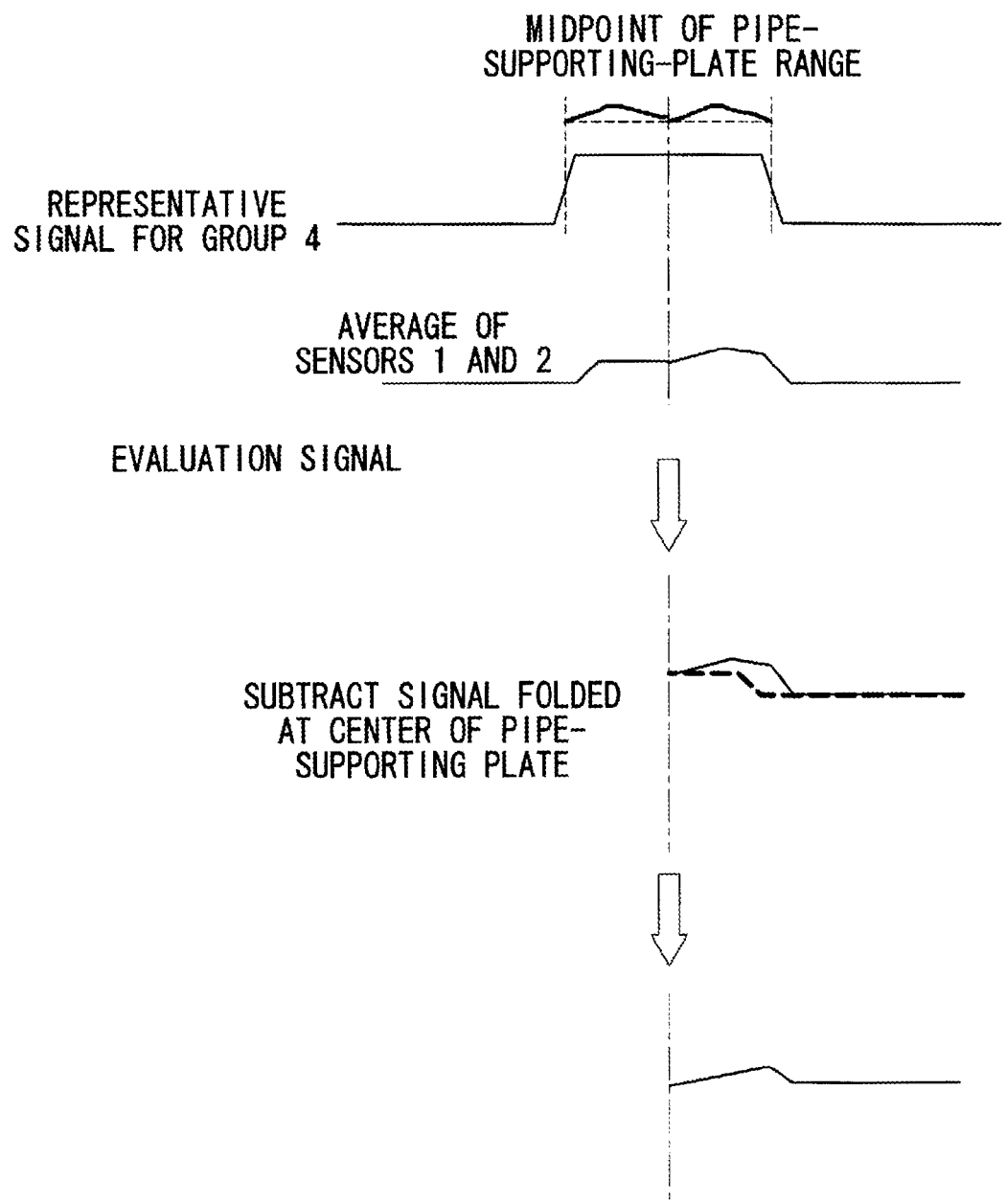

DEPOSIT MEASUREMENT APPARATUS, DEPOSIT MEASUREMENT METHOD, AND COMPUTER-READABLE STORAGE MEDIUM STORING DEPOSIT MEASUREMENT PROGRAM

BACKGROUND OF THE INVENTION

1. Field of the Invention

The present invention relates to a deposit measurement apparatus, a deposit measurement method, and a computer-readable storage medium storing a deposit measurement program that estimate the blockage ratio or the thickness of deposited scale due to scale deposits at a gap between a wall surface of a through-hole and an outer surface of a heat-conducting pipe in a heat exchanger of a steam generator etc., provided with a pipe-supporting plate in which the through-hole for inserting the heat-conducting pipe is formed.

This application is based on Japanese Patent Application No. 2011-001269, the contents of which are incorporated herein by reference.

2. Description of Related Art

For a steam generator, etc. in a pressurized water reactor plant, there is a known method of estimating the amount of iron (II, III) oxide scale deposited on an outer surface of a heat-conducting pipe on the basis of eddy-current flaw detection signals. Particularly in the case in which a pipe hole in a pipe-supporting plate is irregularly shaped, there is a known method of estimating the proportion by which the gap between the heat-conducting pipe and the pipe-supporting plate is blocked by scale (blockage ratio) on the basis of eddy-current flaw detection signals.

As a method of calculating the above-described blockage ratio, there is a generally known method in which a bobbin-coil eddy-current flaw detection probe is employed. In this method, an amplitude in a specific direction is measured based on eddy-current flaw detection signals detected by the bobbin-coil eddy-current flaw detection probe, and a blockage ratio that corresponds to the measured amplitude is obtained from a calibration curve.

Because an eddy current flows in the entire circumferential direction in the bobbin-coil probe described above, for example, it is not possible to separate signals originating from scale at a pipe-supporting-plate gap (a portion where the outer surface of the heat-conducting pipe and the inner surface of the pipe-supporting plate are separated) and signals originating from the pipe-supporting plate. Accordingly, due to differences in positions where the scale is deposited, etc., the waveforms of the eddy-current flaw detection signals become variable even if the blockage ratios are the same; therefore, the precision in estimating the blockage ratio is low.

In order to solve the problem arising from combining the pipe-supporting-plate signals described above, Japanese Unexamined Patent Application, Publication No. 2002-181793 proposes a technique in which an eddy-current flaw detection signal is obtained as a basic signal when there are no deposits; a Lissajous waveform for a deposit signal is obtained by subtracting the basic signal from an eddy-current flaw detection signal for a subject pipe on which deposits collected in an actual apparatus are deposited; and a blockage ratio corresponding to the amplitude thereof is determined from a calibration curve.

BRIEF SUMMARY OF THE INVENTION

Because the amplitude of the pipe-supporting-plate signal is large and its rate of change in the axial direction of the heat-conducting pipe is also large, the pipe-supporting-plate signal cannot be completely removed from the eddy-current flaw detection signal for the pipe-supporting plate to be measured, and a reduction in precision in estimating the blockage ratio due to the influence of the pipe-supporting plate is inevitable, even with the method disclosed in Japanese Unexamined Patent Application, Publication No. 2002-181793.

The present invention provides a deposit measurement apparatus, a deposit measurement method, and a computer-readable storage medium storing a deposit measurement program that are capable of improving precision in estimating the blockage ratio or the thickness of deposited scale in a heat exchanger employing a pipe-supporting plate provided with an irregularly-shaped hole.

A first aspect of the present invention is a deposit measurement apparatus that is applied to a heat exchanger provided with a heat-conducting pipe and a pipe-supporting plate in which a through-hole for inserting the heat-conducting pipe is formed, the through-hole having N protrusions in a circumferential direction of the heat-conducting pipe, and that estimates a blockage ratio of a gap between a wall surface of the through-hole and an outer surface of the heat-conducting pipe or a thickness of a deposit deposited at the gap, the deposit measurement apparatus including a signal acquisition section for acquiring a flaw detection signal by scanning inside the heat-conducting pipe with a sensor; and a processing section for estimating the blockage ratio at the gap or the thickness of the deposit deposited at the gap by using the flaw detection signal for the gap of the pipe-supporting-plate protrusion in the through-hole.

With this configuration, the flaw detection signals are acquired by scanning inside the heat-conducting pipe with the sensor; and, of the acquired flaw detection signals, only the flaw detection signals for the gaps between the wall surface of the through-hole and the outer surface of the heat-conducting pipe are used to estimate the blockage ratios of the gaps or the thicknesses of the deposits deposited at the gaps. In this way, the blockage ratios or the thicknesses of the deposits are estimated by using only the signals in which the influence of the pipe-supporting plate is low; therefore, the influence of the pipe-supporting plate can be reduced, and the precision of estimating the blockage ratios can be improved.

In addition, as disclosed in Japanese Unexamined Patent Application, Publication No. 2002-181793, in a typical method employed to reduce the influence of the pipe-supporting plate, a reference signal for when there is no deposit is prepared in advance, and, when estimating the blockage ratios, the reference signal is subtracted from detected signals, thereby removing the influence of the pipe-supporting plate; however, with this aspect, there is no need to prepare a reference signal in addition to evaluation signals.

The above-described blockage ratio is a ratio of an area where deposit is deposited to the total gap area in a gap between the pipe-supporting plate and the outer surface of the heat-conducting pipe when the through-hole is viewed from the axial direction of the heat-conducting pipe, which can be determined by the following expression.

blockage ratio [%]=(area of deposit/total area of gap)*100

A second aspect of the present invention is a deposit measurement apparatus that is applied to a heat exchanger provided with a heat-conducting pipe and a pipe-supporting plate in which a through-hole for inserting the heat-conducting pipe is formed, the through-hole having a substantially symmetrical shape across a plane that passes through a midpoint of the pipe-supporting plate in an axial direction of the heat-conducting pipe and that perpendicularly intersects with the axial direction of the heat-conducting pipe, and that estimates a blockage ratio of a gap between a wall surface of the through-hole and an outer surface of the heat-conducting pipe or a thickness of a deposit deposited at the gap, the deposit measurement apparatus including a signal acquisition section for acquiring a flaw detection signal by scanning inside the heat-conducting pipe with a sensor; and a processing section for estimating the blockage ratio at the gap or the thickness of the deposit deposited at the gap by using an asymmetrical component of the flaw detection signal across both sides of an axial center position of the pipe-supporting plate.

Scale that becomes deposited on a pipe-supporting portion, which is an irregularly-shaped hole, at the outer surface of the heat-conducting pipe is known to become deposited with a distribution biased in the axial direction of the heat-conducting pipe. Therefore, by utilizing such a characteristic, the blockage ratios or the thicknesses of the deposits are estimated by using the correlation between the asymmetrical components centered on the midpoint of the pipe-supporting plate in the axial direction of the heat-conducting pipe and the blockage ratios. Even though signals to be evaluated are somewhat influenced by the pipe-supporting plate, because the pipe-supporting plate has a substantially symmetrical shape across a plane that passes through the midpoint of the pipe-supporting plate in the axial direction of the heat-conducting pipe and that perpendicularly intersects with the axial direction of the heat-conducting pipe, the influence of the pipe-supporting plate on the detected signals can be reduced by using only the asymmetrical components in the evaluation.

In addition, as disclosed in Japanese Unexamined Patent Application, Publication No. 2002-181793, in a typical method employed to reduce the influence of the pipe-supporting plate, a reference signal for when there is no deposit is prepared in advance, and, when estimating the blockage ratios, the reference signal is subtracted from detected signals, thereby removing the influence of the pipe-supporting plate; however, with this aspect, there is no need to prepare a reference signal in addition to evaluation signals.

With the above-describe deposit measurement apparatus, the signal acquisition section may acquire flaw detection signals when M measurement points disposed inside the heat-conducting pipe at equal intervals in the circumferential direction thereof are scanned in the axial direction of the heat-conducting pipe by scanning with a single or a plurality of sensors provided inside the heat-conducting pipe; and the processing section may include a group-representative-signal calculating section for forming groups so that the flaw detection signals from the measuring points located every M/N measuring points are placed in the same groups and for determining a representative signal for each group; an evaluation-group selection section for specifying protrusion groups that can be considered to be positioned at the pipe-supporting-plate protrusions in the through-hole on the basis of the representative signals and for selecting signals from evaluation groups, which are groups other than the protrusion groups, as evaluation sensor signals; and an estimating section for estimating blockage ratios or thicknesses of deposits by using the evaluation sensor signals.

With the above-described configuration, the flaw detection signals for when M measurement points set inside the heat-conducting pipe at equal intervals in the circumferential direction are scanned in the axial direction of the heat-conducting pipe are acquired by scanning with a single or a plurality of sensors installed inside the heat-conducting pipe; and, with these M flaw detection signals, groups are formed so that the flaw detection signals from the measuring points located every M/N measuring points are placed in the same groups. Accordingly, M eddy-current flaw detection signals are divided into signal groups for the measurement points where the influence of the pipe-supporting plate is large and signal groups for the measurement points where the influence of the pipe-supporting plate is small, that is, signal groups for the measurement points positioned at gaps formed between the protrusions, and M/N groups are formed as a result. Next, in each of the M/N groups, a representative signal is determined by the group-representative-signal calculating section, and protrusion groups that can be considered to be positioned at pipe-supporting-plate protrusions in the through-hole are specified by the evaluation-group selecting section on the basis of the representative signals. Then, the blockage ratios of the gaps or the thicknesses of the deposits are estimated by the estimating section by using the flaw detection signals of the evaluation groups, which are groups other than the protrusion groups. Because the blockage ratios or the thicknesses of the deposits are estimated in this way by using only the signals in which the influence of the pipe-supporting plate is small, the influence of the pipe-supporting plate can be reduced, and the precision of estimating the blockage ratios can be improved.

In the above-described deposit measurement apparatus, the evaluation-group selection section may use the number of sensors positioned in an angular range affected by the protrusions as an exclusion number, may specify the same number of representative signals as the exclusion number, and may specify groups to which the specified representative signals belong as the protrusion groups.

Because the angular range affected by the pipe-supporting-plate protrusions is determined in advance, and the number of measurement points positioned in the angular range is stored, groups that are influenced by the pipe-supporting-plate protrusions are easily specified.

In the above-described deposit measurement apparatus, of the representative signals, the processing section may specify a midpoint in a pipe-supporting plate region for the representative signals that are judged to be positioned in the angular range affected by the protrusions; may specify a position in each flaw detection signal of the evaluation groups that is the same as the midpoint; may fold each flaw detection signal using the specified position as an axial center; may acquire difference signals between folded signals and non-folded signals, thereby determining respective asymmetrical components centered on the midpoints of the flaw detection signals; and may estimate blockage ratios or thicknesses of deposits at gaps on the basis of a plurality of the asymmetrical components.

With such a configuration, because the midpoint of the pipe-supporting plate region is specified by using representative signals judged to be positioned in the angular range affected by the protrusions, in other words, flaw detection signals positioned at the pipe-supporting-plate protrusions, the midpoint of the pipe-supporting plate can be precisely specified. In particular, if the midpoint of the pipe-supporting-plate region is specified by using a representative signal with the largest amplitude, the midpoint of the pipe-supporting plate can be specified most precisely.

Then, the midpoint is reflected in each of the flaw detection signals of the evaluation groups; the signals are folded with the midpoint as the center; and difference signals between the folded signals and non-folded signals are acquired, thereby individually determining asymmetrical components centered on the pipe-supporting-plate midpoint. Because the blockage ratios or the thicknesses of the deposits are estimated by using the difference signals, the influence of the pipe-supporting plate on the detected signals can be reduced, and the precision of estimating the blockage ratios can be further improved.

In the above-described deposit measurement apparatus, of the representative signals, the processing section may specify a midpoint in a pipe-supporting plate region for the representative signals that are judged to be positioned in the angular range affected by the protrusion; may specify a position in an evaluation signal obtained from each flaw detection signal of the evaluation groups that is the same as the midpoint; may fold each evaluation signal using the specified position as an axial center; may acquire difference signals between folded signals and non-folded signals, thereby determining respective asymmetrical components centered on the midpoints of the evaluation signals; and may estimate blockage ratios or thicknesses of deposits at gaps on the basis of a plurality of the asymmetrical components.

With such a configuration, because the midpoint of the pipe-supporting plate region is specified by using representative signals judged to be positioned in the angular range affected by the protrusions, in other words, flaw detection signals positioned at the pipe-supporting-plate protrusions, the midpoint of the pipe-supporting plate can be precisely specified. In particular, if the midpoint of the pipe-supporting-plate region is specified by using a representative signal with the largest amplitude, the midpoint of the pipe-supporting plate can be specified most precisely.

Then, the midpoint is reflected in the evaluation signals obtained from each of the flaw detection signals of the evaluation groups; the signals are folded with the midpoint as the center; and difference signals between the folded signals and non-folded signals are acquired, thereby individually determining asymmetrical components centered on the pipe-supporting-plate midpoint. Because the blockage ratios or the thicknesses of the deposits are estimated by using the difference signals, the influence of the pipe-supporting plate on the detected signals can be reduced, and the precision of estimating the blockage ratios can be further improved.

The above-described evaluation signals include, for example, an average flaw detection signal wherein the flaw detection signals are averaged.

In the above-described deposit measurement apparatus, signals acquired by the signal acquisition section may be signals acquired by an eddy-current flaw detection system in which a signal factor originating from a magnetic material is added to a correction test piece, and a correction may be performed by using a signal obtained with the correction test piece as a reference signal.

In the case where scale deposited on the heat-conducting pipe and the pipe-supporting plate is magnetic material, signals originating from the scale are mainly signals generated due to magnetic permeability variation. Therefore, detected signals in which the scale signals are stable can be acquired by performing signal correction by using a signal factor originating from the magnetic permeability variation instead of signals involving deforming of the heat-conducting pipe or the addition of a slit.

A third aspect of the present invention is an eddy-current inspection method of performing detection by employing any one of deposit measurement apparatus described above.

A fourth aspect of the present invention is a deposit measurement method that is applied to a heat exchanger provided with a heat-conducting pipe and a pipe-supporting plate in which a through-hole for inserting the heat-conducting pipe is formed, the through-hole having N protrusions in a circumferential direction of the heat-conducting pipe, and that estimates a blockage ratio of a gap between a wall surface of the through-hole and an outer surface of the heat-conducting pipe or thickness of a deposit deposited at the gap, the deposit measurement method including a step of acquiring a flaw detection signal by scanning inside the heat-conducting pipe with a sensor; and a step of estimating the blockage ratio at the gap or the thickness of the deposit deposited at the gap by using the flaw detection signal for the gap of the pipe-supporting-plate protrusion in the through-hole.

A fifth aspect of the present invention is a deposit measurement method that is applied to a heat exchanger provided with a heat-conducting pipe and a pipe-supporting plate in which a through-hole for inserting the heat-conducting pipe is formed, the through-hole having a substantially symmetrical shape across a plane that passes through a midpoint of the pipe-supporting plate in an axial direction of the heat-conducting pipe and that perpendicularly intersects with the axial direction of the heat-conducting pipe, and that estimates a blockage ratio of a gap between a wall surface of the through-hole and an outer surface of the heat-conducting pipe or a thickness of a deposit deposited at the gap, the deposit measurement method including a step of acquiring a flaw detection signal by scanning inside the heat-conducting pipe with a sensor; and a step of estimating the blockage ratio at the gap or the thickness of the deposit deposited at the gap by using an asymmetrical component of the flaw detection signal across both sides of an axial center position of the pipe-supporting plate.

A sixth aspect of the present invention is a computer-readable storage medium that stores a deposit measurement program that is applied to a heat exchanger provided with a heat-conducting pipe and a pipe-supporting plate in which a through-hole for inserting the heat-conducting pipe is formed, the through-hole having N protrusions in a circumferential direction of the heat-conducting pipe, and that estimates a blockage ratio of a gap between a wall surface of the through-hole and an outer surface of the heat-conducting pipe or a thickness of a deposit deposited at the gap, the computer-readable storage medium storing the deposit measurement program for causing a computer to execute processing for acquiring a flaw detection signal by scanning inside the heat-conducting pipe with a sensor; and processing for estimating the blockage ratio at the gap or the thickness of the deposit deposited at the gap by using the flaw detection signal for the gap of the pipe-supporting-plate protrusion in the through-hole.

A seventh aspect of the present invention is a computer-readable storage medium that stores a deposit measurement program that is applied to a heat exchanger provided with a heat-conducting pipe and a pipe-supporting plate in which a through-hole for inserting the heat-conducting pipe is formed, the through-hole having a substantially symmetrical shape across a plane that passes through a midpoint of the pipe-supporting plate in an axial direction of the heat-conducting pipe and that perpendicularly intersects with the axial direction of the heat-conducting pipe, and that estimates a blockage ratio of a gap between a wall surface of the through-hole and an outer surface of the heat-conducting pipe or a thickness of a deposit deposited at the gap, the computer-readable storage medium storing the deposit measurement program for causing a computer to execute processing for acquiring a flaw detection signal by scanning inside the heat-conducting pipe with a sensor; and processing for estimating the blockage ratio at the gap or the thickness of the deposit deposited at the gap by using an asymmetrical component of the flaw detection signal across both sides of an axial center position of the pipe-supporting plate.

BRIEF DESCRIPTION OF THE SEVERAL VIEWS OF THE DRAWINGS

FIG. 13 is an explanatory diagram for explaining processing performed at an evaluation-signal generating section shown in FIG. 11.

FIG. 14 is an explanatory diagram for explaining other processing performed at the evaluation-signal generating section shown in FIG. 11.

DETAILED DESCRIPTION OF THE INVENTION

First Embodiment

A deposit measurement apparatus, a deposit measurement method, and a computer-readable storage medium in which a deposit measurement program is stored, according to a first embodiment of the present invention, will be described below. Here, a description will be given for the case in which the present invention is applied to a heat exchanger having a pipe-supporting plate in which a plurality of through-holes for inserting heat-conducting pipes are formed and a plurality of heat-conducting pipes that are inserted into the through-holes in the pipe-supporting plate. In addition, although a case of estimating a blockage ratio due to scale deposits at a gap between wall surfaces of the through-holes and outer surfaces of the heat-conducting pipes will be described in the following description, the thickness of the deposits may be measured instead of the blockage ratio. Because the blockage ratio is determined by dividing the areas of the deposits by the total area of the gap, with regard to the case where the blockage ratio is determined and the case where the thickness of the deposits is determined, the effects thereof are the same.

Figure 1:
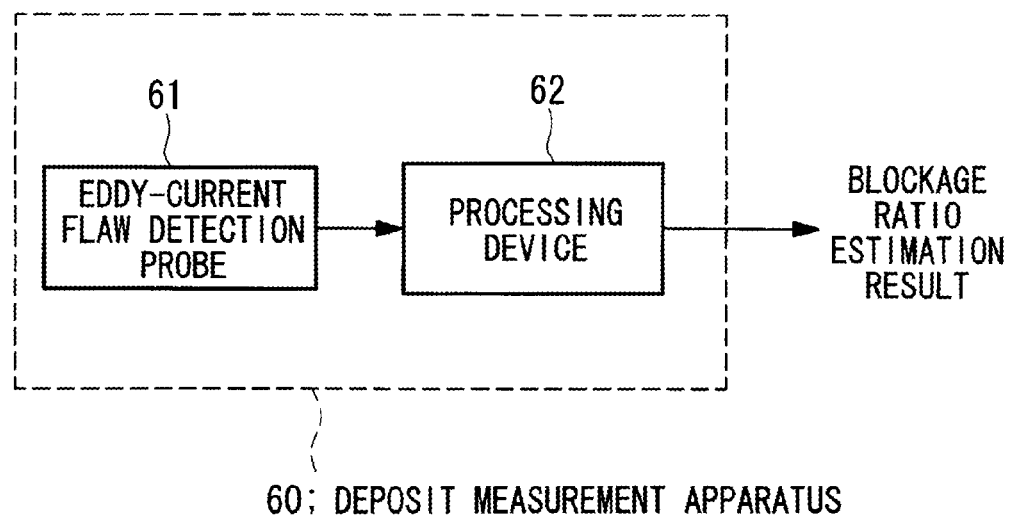
FIG. 1 is a diagram showing, in outline, the configuration of a deposit measurement apparatus according to a first embodiment of the present invention.

FIG. 1 is a diagram showing, in outline, the configuration of a deposit measurement apparatus according to this embodiment. As shown in FIG. 1, a deposit measurement apparatus 60 is provided with a multi-sensor eddy-current flaw detection probe (a signal acquisition section) 61 and a processing device 62 that processes eddy-current flaw detection signals acquired by the eddy-current flaw detection probe 61.

Figure 2:
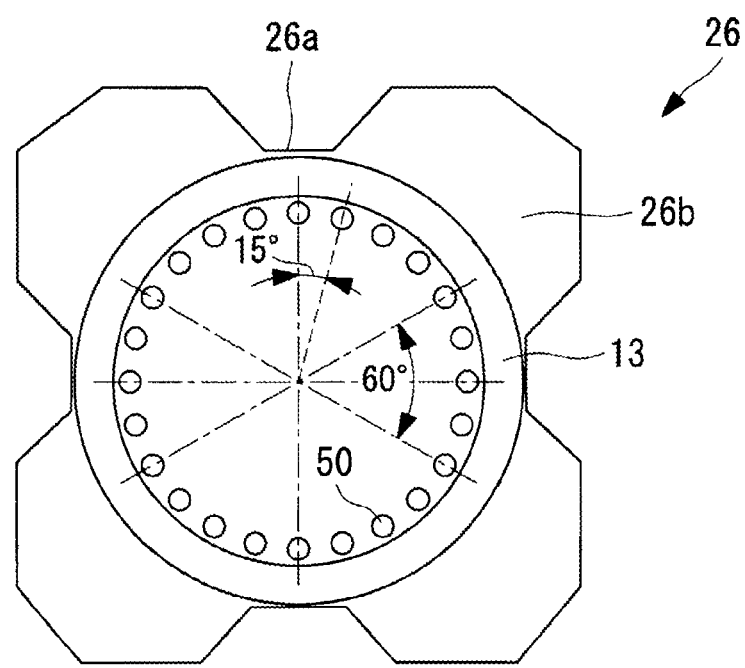
FIG. 2 is a schematic diagram of a through-hole through which heat-conducting pipe is inserted, viewed from the axial direction of the heat-conducting pipe.
Figure 3:
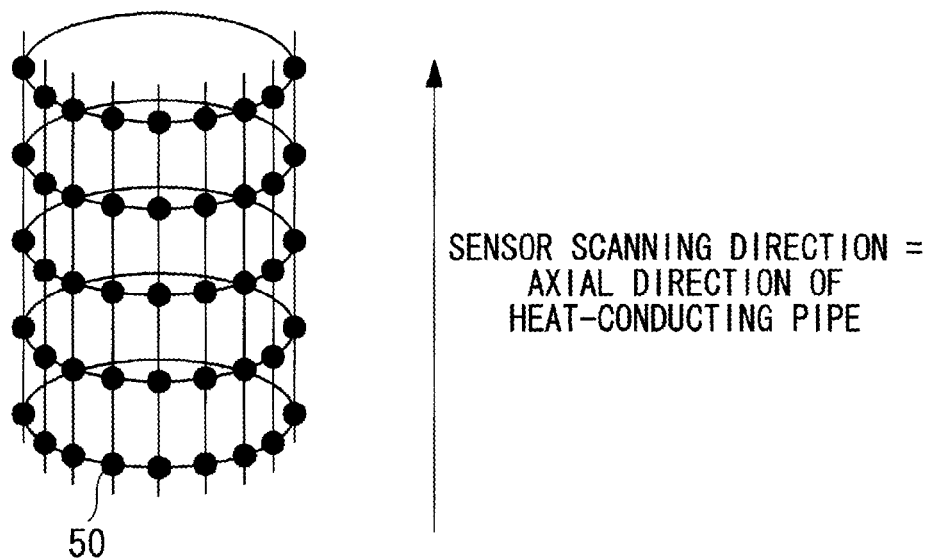
FIG. 3 is a diagram for explaining a signal obtained with an eddy-current flaw detection probe.

FIG. 2 is a schematic diagram of a through-hole 26 through which a heat-conducting pipe 13 is inserted, viewed from the axial direction of the heat-conducting pipe. As shown in FIG. 2, the through-hole 26 according to this embodiment has four protrusions 26a in the circumferential direction of the heat-conducting pipe 13. The deposit measurement apparatus 60 mainly estimates blockage ratios of gaps 26b that are formed between the protrusions 26a and that exist between the wall surface of the through-hole and the outer surface of the heat-conducting pipe. As shown in a conceptual diagram in FIG. 3, for example, by scanning inside the heat-conducting pipe 13 with a sensor or a plurality of sensors, eddy-current flaw detection signals are acquired for when measurement points set at substantially equal intervals in the circumferential direction of the heat-conducting pipe 13 are scanned in the axial direction of the heat-conducting pipe 13.

In this embodiment, 24 measurement points are set; 24 sensors are disposed at the same positions as these measurement points; and eddy-current flaw detection signals are acquired by scanning these sensors in the axial direction of the heat-conducting pipe 13. That is, the eddy-current flaw detection signals are acquired by scanning, in the axial direction of the heat-conducting pipe 13, a multi-sensor eddy-current flaw detection probe in which the 24 sensors are arranged next to each other in the circumferential direction of the heat-conducting pipe 13 at substantially equal intervals (at about 15° intervals in the circumferential direction).

Although an example in which the number of measurement points is 24 is described in this embodiment, the number of measurement points is not particularly limited. It is desirable that the number of measurement points be an integral multiple of the number of circumferential-direction protrusions in the through-hole; however, in the case where the number of measurement points is not an integral multiple of the number of protrusions, similar signals can be obtained by performing interpolation so as to make the number of circumferential-direction measurement points for the acquired signals an integral multiple of the number of protrusions.

In addition, because numerous sensors are densely aced in the circumferential direction, it is difficult to arrange the sensors in a single row in the case of a multi-sensor probe, and thus there are probes in which sensors are disposed by being divided into multiple rows; however, if axial intervals between the sensor rows and axial intervals between the signal measurement points are known, the axial positions of the signals can be corrected to make the measurement points equivalent to those for which sensors are arranged in a single row.

Figure 4:
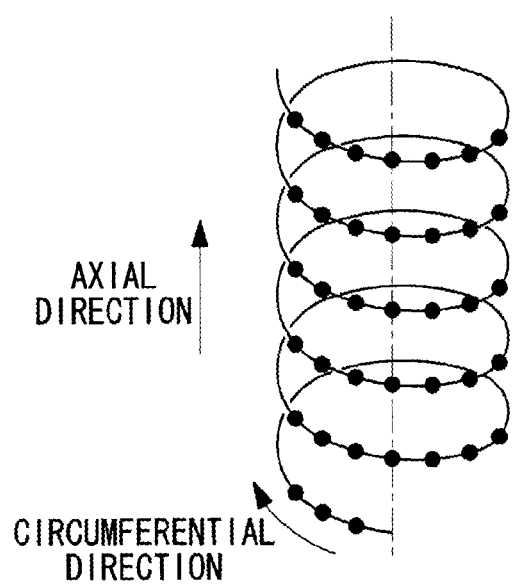
FIG. 4 is a diagram for explaining a method for obtaining eddy-current flaw detection signals with an eddy-current flaw detection probe provided with a sensor when individual measurement points are scanned in the axial direction of the heat-conducting pipe.

As shown in FIG. 4, equivalent signals may also be acquired by scanning the heat-conducting pipe in the axial direction while rotating a probe having a single sensor, instead of a multi-sensor probe, in the circumferential direction of the heat-conducting pipe, in and by interpolating the signals acquired at this time. In this way, the configuration of the sensor for acquiring the eddy-current flaw detection signals at the individual measurement points is not particularly limited.

Furthermore, the interpolation of the measurement points can be performed with a generally known method, such as linear interpolation or the like. Similar effects can be obtained by treating such interpolated measurement points as sensors, described below.

In addition, the eddy-current flaw detection signals from the eddy-current flaw detection probe 61 are preferably corrected by employing a correction method for estimating the blockage ratio. Normally, in an eddy-current flaw detection probe employed in flaw detection, a flaw signal (for example, a signal from a full-circumference slit or the like) or a deformation signal is employed as a signal-correction reference; however, because deposits are associated with magnetic permeability variation, correction in which a signal factor associated with magnetic permeability variation is used as the reference is more appropriate for evaluating a deposit signal than correction with a signal factor that is not associated with magnetic permeability variation.

Specifically, a magnetic material is added to a correction test piece to be used as a reference for correction. This includes, for example, attaching a circular-hole pseudo-pipe-supporting plate, a magnetic ring, a magnetic foil, etc. Normally, a circular-hole pipe-supporting plate is typically attached to a correction test piece of an eddy-current flaw detection probe for multifrequency computation; therefore, correction for estimating the blockage ratio can also be performed by using this plate without using a special correction test piece.

The 24 eddy-current flaw detection signals acquired by the sensors are transferred to the processing device 62 (see FIG. 1) to be processed.

Figure 5:
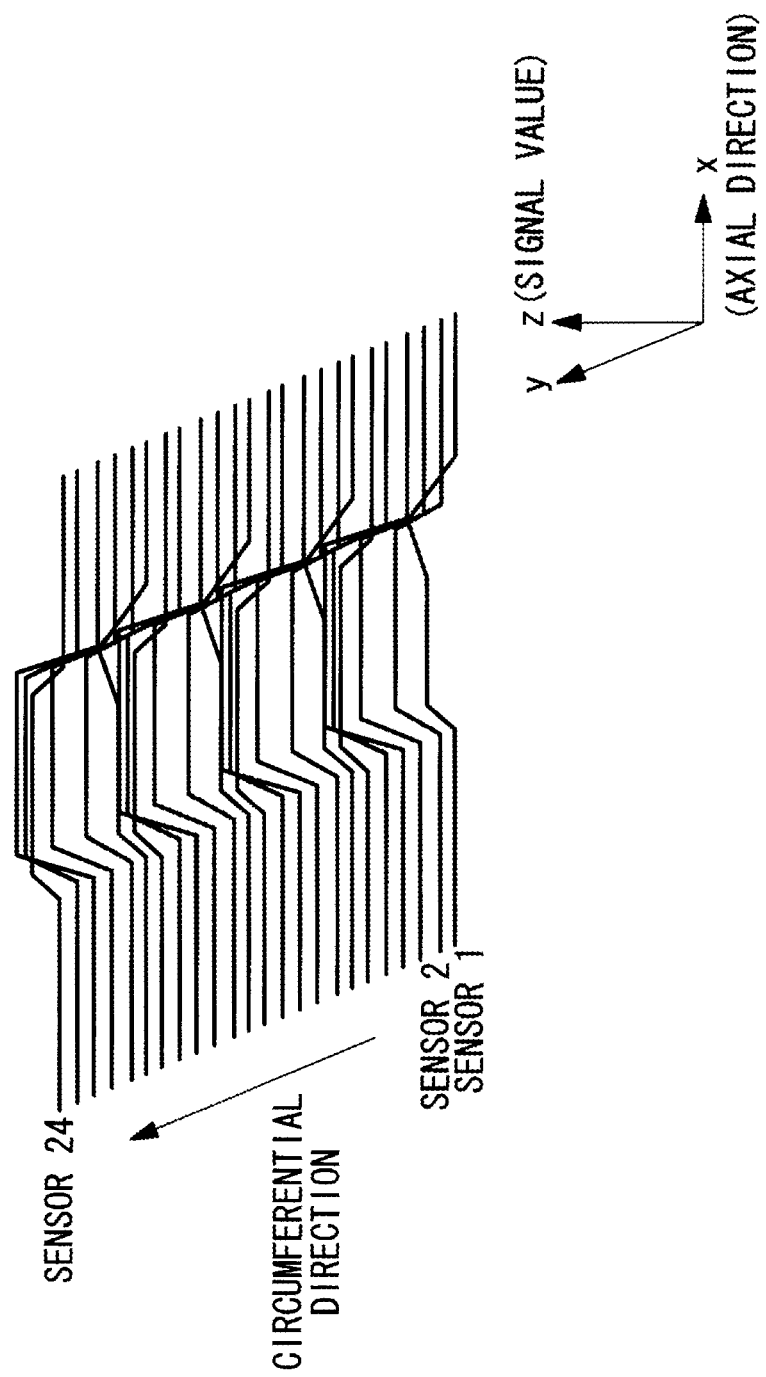
FIG. 5 is a diagram showing examples of eddy-current flaw detection signals acquired with the individual sensors provided in the eddy-current flaw detection probe.

FIG. 5 is a diagram showing examples of the eddy-current flaw detection signals acquired with the sensors. In FIG. 5, the x-axis is time (i.e., detection positions in the axial direction of the heat-conducting pipe), the y-axis is sensor number (i.e., detection positions in the circumferential direction of the heat-conducting pipe), and the z-axis is signal values.

Note that, in the case of the eddy-current flaw detection, the signal values are complex numbers; however, in order to explain the concept, either the real component or the imaginary component is represented in FIG. 5. In addition, with regard to the sensor number, a reference sensor is arbitrarily set and, by using this sensor as sensor number "1", sensor numbers are sequentially assigned, clockwise therefrom.

The processing device 62 is a computer system (calculator system) provided with a CPU (Central Processing Unit), a main storage device, such as RAM (Random Access Memory), etc., an auxiliary storage device, a communication device that sends and receives information by communicating with external equipment, and so on. The auxiliary storage device, which is a computer-readable storage medium, is, for example, a magnetic disk, a magneto-optical disk, a CD-ROM, a DVD-ROM, a semiconductor memory, etc. Various programs (for example, a blockage-ratio estimation program) are stored in the auxiliary storage device; the CPU loads the programs into the main storage device from the auxiliary storage device and executes them to realize various kinds of processing.

Figure 6:
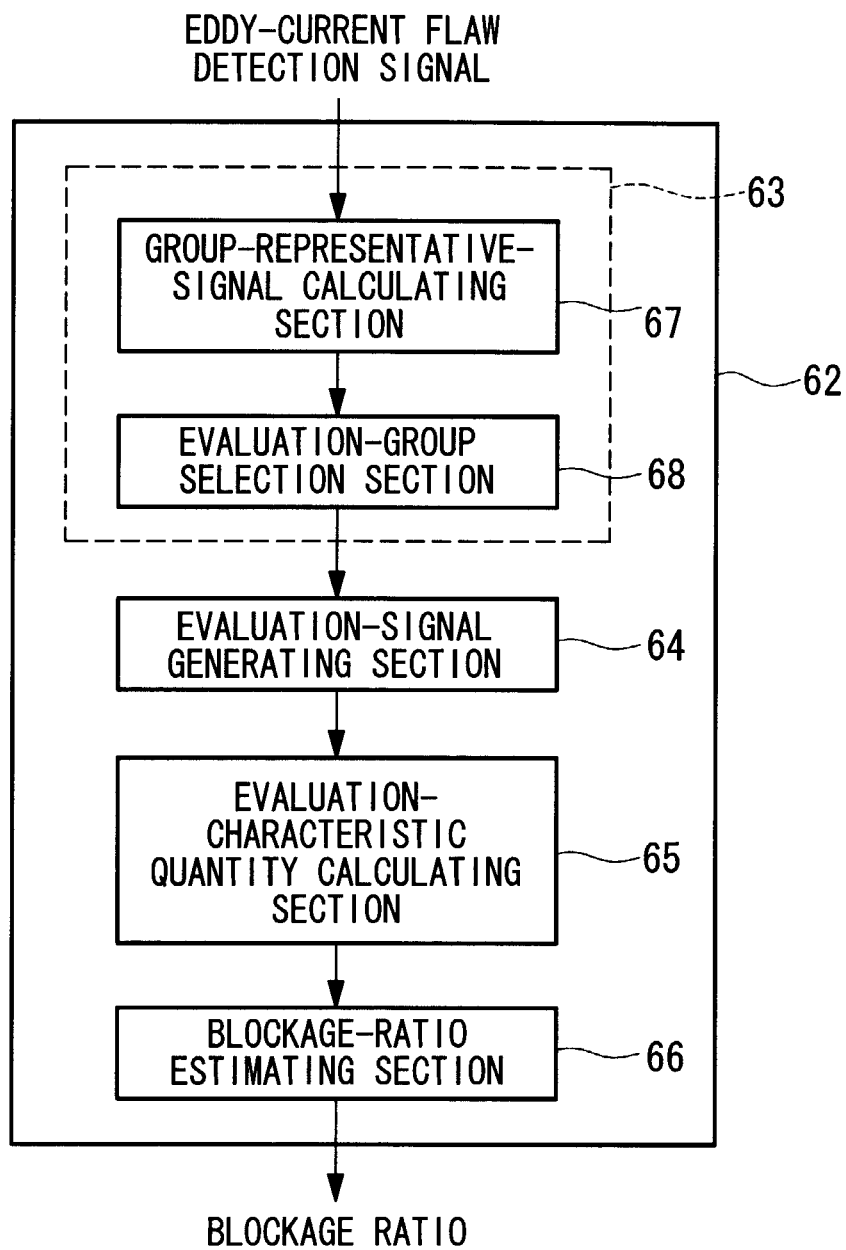
FIG. 6 is a functional block diagram showing, in expanded form, functions provided in a processing device shown in FIG. 1.

FIG. 6 is a functional block diagram showing, in expanded form, functions provided in the processing device 62. As shown in FIG. 6, the processing device 62 is provided with an evaluation-sensor selecting section 63, an evaluation-signal generating section 64, an evaluation-characteristic-quantity calculating section 65, and a blockage-ratio estimating section (an estimating section) 66, and the evaluation-sensor selecting section 63 is provided with a group-representative signal calculating section 67 and an evaluation-group selecting section 68.

The group-representative signal calculating section 67 in the evaluation-sensor selecting section 63 divides the measurement points into groups on the basis of the number (M/N) obtained by dividing the number of measurement points 50, i.e., M, by the number of protrusions 26*a* provided in the through-hole 26, i.e., N, so that the measurement points 50 located every M/N measurement points are placed in the same group. Because there are 24 measurement points 50 and 4 protrusions 26*a* in this embodiment, the measurements points that are located every 6 (i.e., 24/4) measurement points are placed in the same group. Accordingly, 24 eddy-current flaw detection signals shown in FIG. 5 are divided into six groups as follows.

Group 1: sensor 1, sensor 7, sensor 13, sensor 19
Group 2: sensor 2, sensor 8, sensor 14, sensor 20
Group 3: sensor 3, sensor 9, sensor 15, sensor 21
Group 4: sensor 4, sensor 10, sensor 16, sensor 22
Group 5: sensor 5, sensor 11, sensor 17, sensor 23
Group 6: sensor 6, sensor 12, sensor 18, sensor 24

Next, a representative signal is determined for each group. For example, an average signal is determined for each group, and the average signal is used as the representative signal for each group. Note that, in addition to the average signal, a signal having the largest amplitude in a group may be used as a representative signal.

On the basis of the representative signals, the evaluation-group selecting section 68 specifies protrusion groups that can be considered to be positioned at the pipe-supporting-plate protrusions 62*a* in the through hole 62; based on this, specifies groups that can be considered to be positioned at the gaps; and selects them as groups to be used for blockage-ratio evaluation. Specifically, first, the evaluation-group selecting section 68 uses the number of sensors positioned in an angular range affected by the pipe-supporting-plate protrusions 26*a* in the through-hole 26 as the exclusion number; the representative signals in a number corresponding to the exclusion number are specified from those signals having larger amplitudes; and the groups to which the specified representative signals belong are specified as the protrusion groups.

Figure 7:
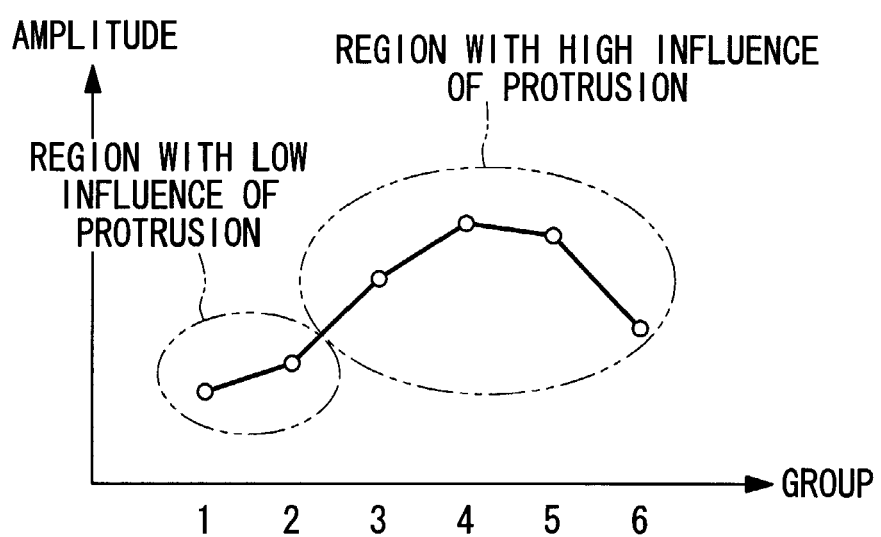
FIG. 7 is a diagram for explaining a method for specifying a protrusion group with an evaluation-group selecting section.

For example, in the case where the angular range affected by the protrusions 26*a* is 60°, because the sensors are disposed at 15° intervals in this embodiment, the exclusion number is 4 (i.e. 60°/15°. Therefore, the evaluation-group selecting section 68 specifies 4 representative signals in order from those having larger amplitudes and specifies the groups to which the specified representative signals belong as the protrusion groups. Here, the groups at both ends (in this example, Group 1 and Group 6) are treated as being consecutive. The above description "specifies 4 representative signals in order from those having larger amplitudes" means that a sensor for which the above-described amplitude is the largest is selected first; of the sensors on both sides thereof, one having a larger amplitude is specified as the second; one on the opposite side therefrom is specified as the third; and, furthermore, one opposite therefrom is specified as the fourth. For instance, in the example shown in FIG. 7, the amplitude is the largest for Group 4; when Group 3 and Group 5, which are on both sides thereof, are compared, Group 5 is larger, and thus, Group 5 is specified as the second; Group 3, which is opposite from Group 5, is specified as the third; Group 6 opposite therefrom is specified as the fourth; and thus, Groups 3 to 6 are specified as the protrusion groups.

Next, the eddy-current flaw detection signals of the evaluation groups, which are groups other than the protrusion groups, are selected as gap groups, and the sensors that belong to the gap groups are selected as evaluation sensors. Specifically, in the example in FIG. 7, the sensors that belong to Groups 1 and 2 are selected as the evaluation sensors.

The evaluation-signal generating section 64 generates signals to be used for estimating blockage ratios by using the signals from the selected sensors. For example, in the case where the blockage ratios are separately estimated for each of the four gaps 26b provided in the through hole 26, the evaluation-signal generating section 64 reorganizes the evaluation signals into collections of sensors for each gap. Specifically, Groups 1 and 2, which are the evaluation groups, are reorganized as follows.

Group A: sensor 1, sensor 2
Group B: sensor 7, sensor 8
Group C: sensor 13, sensor 14
Group D: sensor 19, sensor 20

In addition, in order to determine an average blockage ratio for the four gaps 26b, an average is determined for all eddy-current flaw detection signals of the evaluation groups, and this average is used as an evaluation signal.

The evaluation-characteristic-quantity calculating section 65 determines the amplitude of the evaluation signal and uses it as a blockage-ratio-estimating characteristic quantity.

Figure 8A:
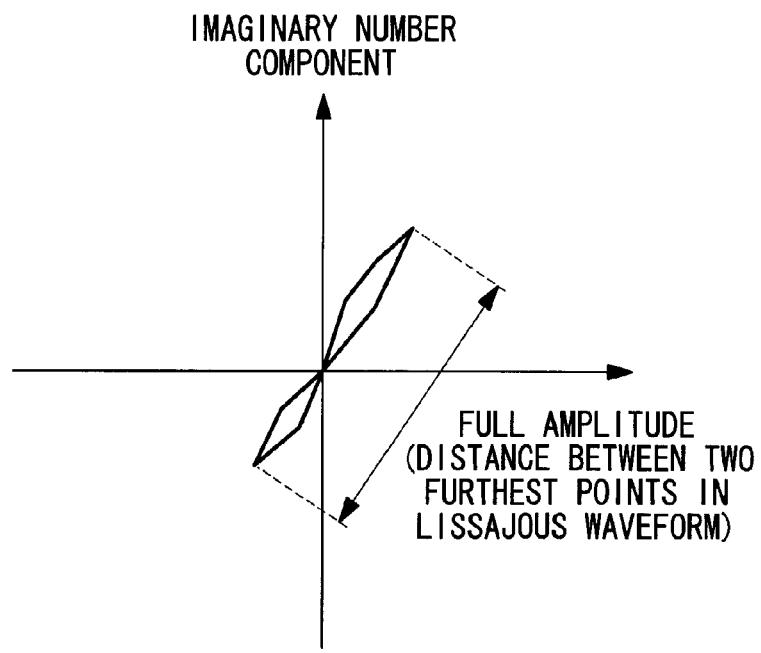
FIG. 8A and FIG. 8B are diagrams for explaining the manner in which the amplitude of an eddy-current flaw detection signal is determined.
Figure 8B:
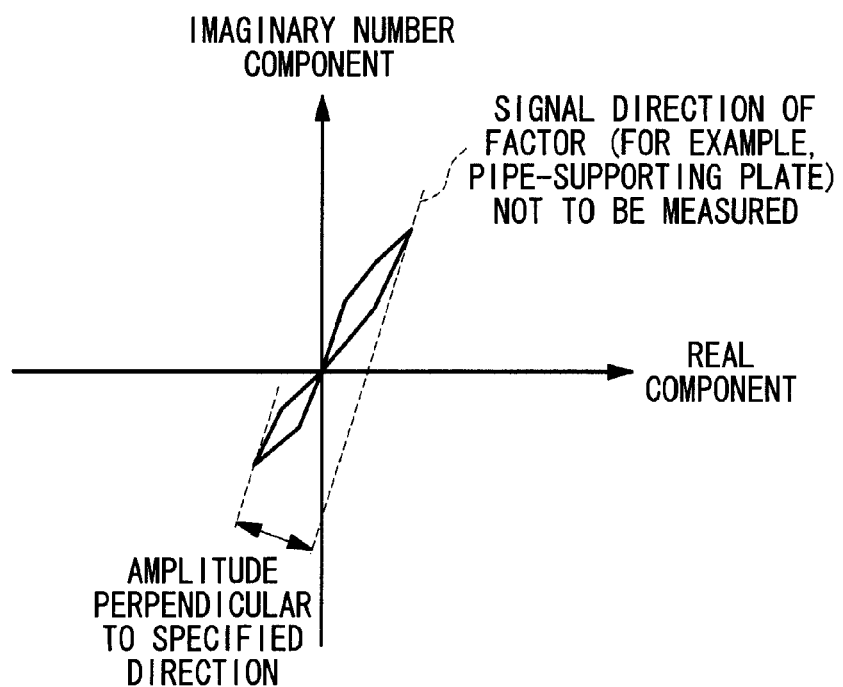

As shown in FIG. 8A, methods of determining the amplitudes of the eddy-current flaw detection signals include, for example, a method in which the distance between the furthest two points in a Lissajous waveform (a waveform displayed when the real component of the measurement signal is set on the horizontal axis and the imaginary component of the measurement signal is set on the vertical axis) is determined as the amplitude; a method in which, as shown in FIG. 8B, the direction of signals due to a factor (for example, the pipe-supporting plate) not to be measured is determined, and the amplitude in the direction orthogonal to that direction is employed as the amplitude; a method in which the amplitude of the signal from which the basic signal has been subtracted is employed, as disclosed in Japanese Unexamined Patent Application, Publication No. 2002-181793; and so on.

In addition, there may be multiple types of characteristic quantities. That is, multiple types of amplitudes may be employed as the characteristic quantities, and it is also permissible to add to the characteristic quantity a characteristic that potentially affects the amplitude, other than the blockage ratio, such as the axial distribution length of the signal.

Figure 9:
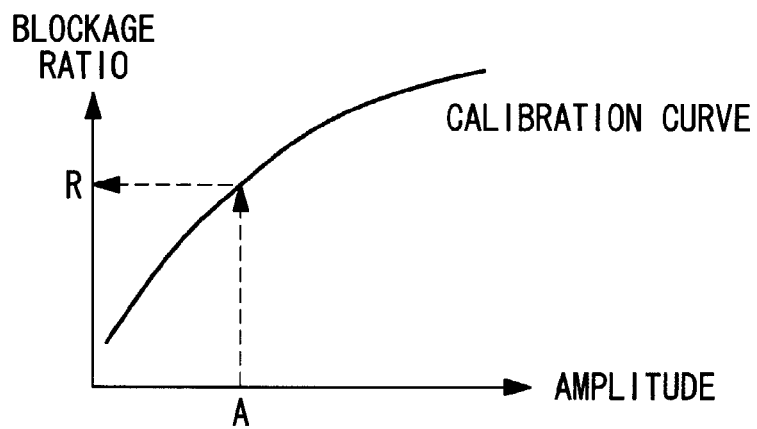
FIG. 9 is a diagram showing an example calibration curve.

At the blockage-ratio estimating section 66, the blockage ratio is determined by using a calibration curve such as one shown in FIG. 9, which is prepared in advance. FIG. 9 shows an example calibration curve for the case in which the blockage ratio is estimated by using a single type of characteristic quantity (amplitude); however, in the case where multiple types of characteristic quantities are employed, the blockage ratio is determined by using an equation prepared in advance.

The calibration curve or the equation is obtained by determining the above-described characteristic quantity by using data from an actual apparatus or a plurality of test pieces for each of which the blockage ratios are known in advance and by determining an optimal equation for calculating the blockage ratio from the characteristic quantity. Methods for determining the optimal equation include known methods such as the least squares method (regression analysis), neutral networks, genetic algorithms, etc., and, by using the blockage ratio as an objective variable (output) and the characteristic quantity as an explanatory variable (input), an optimal equation in which errors are minimized for an estimated blockage ratio is calculated from the above-described known blockage ratios and the characteristic quantity.

As has been described above, with the deposit measurement apparatus, the deposit measurement method, and the computer-readable storage medium in which the deposit measurement program is stored, because the blockage ratios are estimated using only the signals for which the influence of the pipe-supporting plate is low, the influence of the pipe-supporting plate can be reduced, and the precision in estimating blockage ratios can be improved.

Note that the description herein has been given for a method in which the signals that correspond to the pipe-supporting-plate protrusions and gaps in the through-hole are selected by employing grouping; however, the method for selecting the gaps is not limited thereto. For example, in the case where signals can be associated with protrusions or gaps in the through hole with supplementary sensors, signals corresponding to the gaps may be selected by using these sensors.

Note that, in the case where the thickness of the deposits is estimated instead of the blockage ratio, a deposit-thickness estimating section is provided instead of the blockage-ratio estimating section; a calibration curve is prepared in which amplitudes and deposit thickness are associated with each other by using a method similar to the one described above; and the deposit thickness is determined using the calibration curve. Naturally, the characteristic quantities may be of multiple types; specifically, multiple types of amplitudes may be employed as the characteristic quantities, and it is also permissible to add to the characteristic quantity a characteristic that potentially affects the amplitude, other than the deposit thickness, such as the axial distribution length of the signal.

Second Embodiment

Next, a deposit measurement apparatus, a deposit measurement method, and a computer-readable storage medium, in which a deposit measurement program is stored, according to a second embodiment of the present invention, will be described.

In the second embodiment, a description will be given of a case in which the deposit measurement apparatus, the deposit measurement method, and the computer-readable storage medium in which the deposit measurement program is stored are applied to a heat exchanger whose heat-conducting-pipe through-hole in a pipe-supporting plate have a symmetrical shape across the midpoint of the pipe-supporting plate in the axial direction of the heat-conducting pipe.

Figure 10:
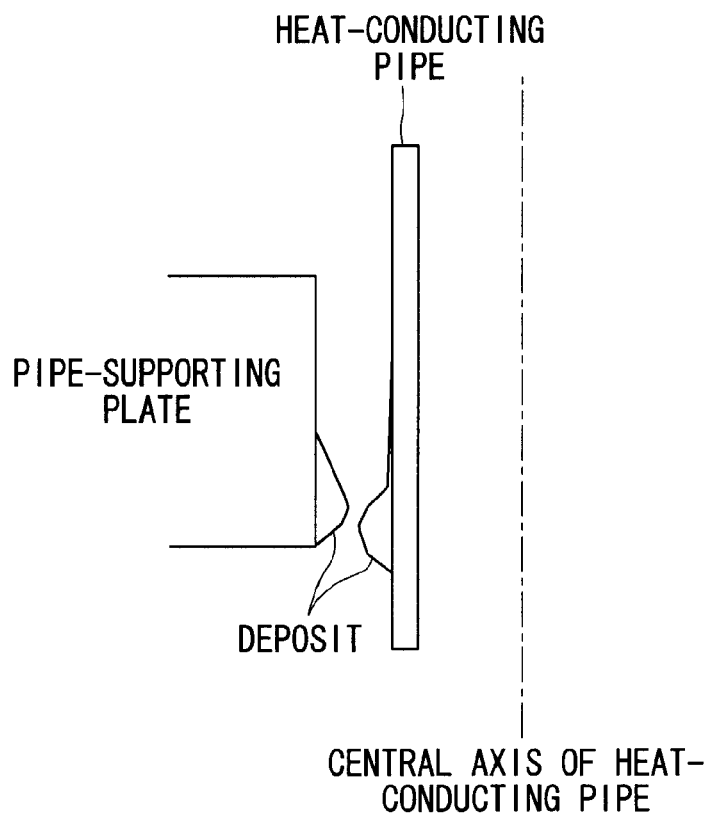
FIG. 10 is a diagram for explaining characteristics of scale that is deposited on outer surfaces of a pipe-supporting plate and a heat-conducting pipe.

As shown in FIG. 10, the scale that becomes deposited on the outer surface of the heat-conducting pipe in the pipe-supporting plate is known to become deposited on the pipe-supporting plate with a bias in the axial direction of the heat-conducting pipe. In the case where the deposits are deposited in the way described above, in this embodiment, the blockage ratios are estimated by using asymmetry in signals across both sides of a midpoint in the thickness direction of the pipe-supporting plate based on characteristics of deposition behaviors.

Figure 11:
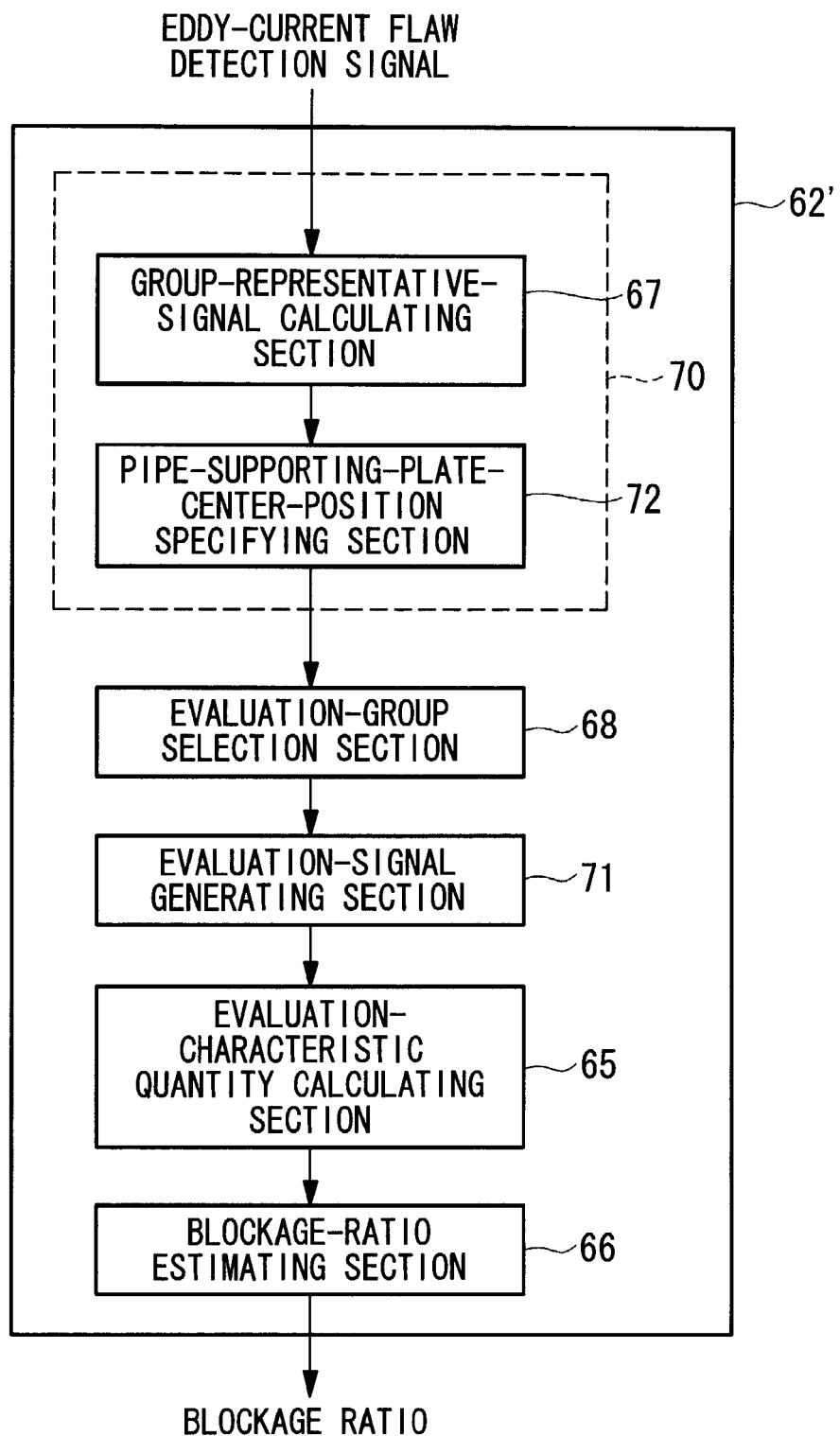
FIG. 11 is a functional block diagram showing, in expanded manner, functions provided in a processing device in a deposit measurement apparatus according to a second embodiment of the present invention.

FIG. 11 is a functional block diagram showing, in expanded manner, functions provided in a processing device 62' according to this embodiment. As shown in FIG. 11, the processing device 62' has a substantially similar configuration to that in the first embodiment described above; however, there is a difference in that a pipe-supporting-plate position specifying section 70 is added, and specifics of the processing at an evaluation-signal generating section 71 differ from those of the evaluation-signal generating section 64 according to the above-described first embodiment. Note that the same reference signs are given to structures that are the same as those in the first embodiment described above.

The processing procedure of the processing device 62' according to this embodiment will be described below.

As shown in FIG. 11, the pipe-supporting-plate position specifying section 70 is provided with the group-representative-signal calculating section 67 and a pipe-supporting-plate-center-position specifying section 72. Because the group-representative-signal calculating section 67 is the same as that in the first embodiment, a description thereof will be omitted. Of the group representative signals determined by the group-representative-signal calculating section 67, a group with the largest amplitude is selected as a pipe-supporting-plate-region inspection signal at the pipe-supporting-plate-center-position specifying section 72, assuming that it is a group in which the influence of the pipe-supporting-plate protrusions in the through-hole is the greatest.

Figure 12:
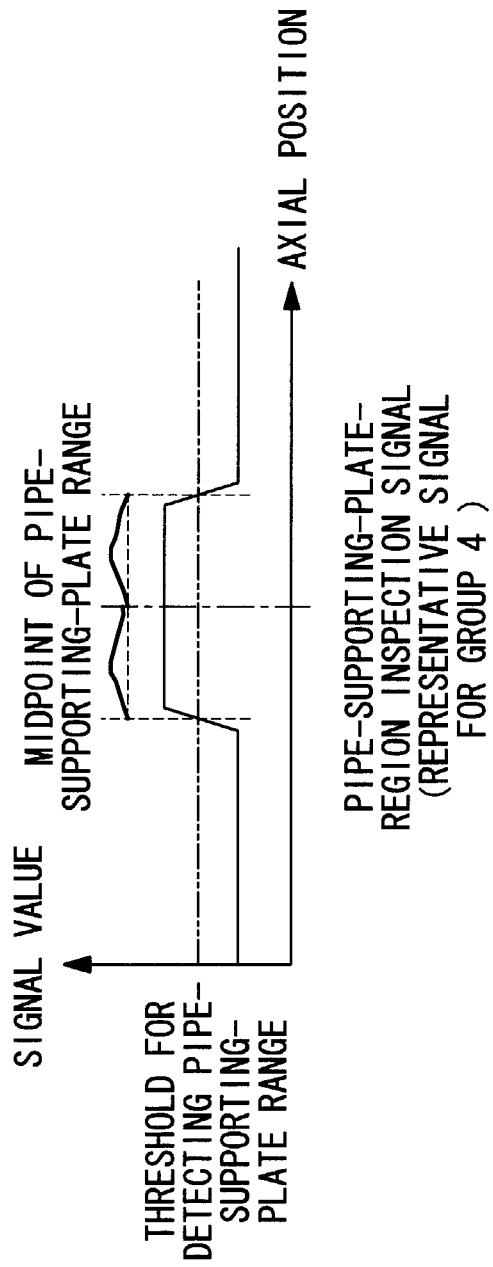
FIG. 12 is an explanatory diagram for explaining processing performed at a pipe-supporting-plate position specifying section shown in FIG. 11.

Next, an axial region of the pipe-supporting-plate signal is specified by using the selected pipe-supporting-plate-region inspection signal, and the midpoint thereof is determined to be a pipe-supporting-plate center position. As shown in FIG. 12, the region is specified by a method such as determining a region where signal values are equal to or greater than a threshold. The threshold may be a predetermined constant, or a value obtained by multiplying the maximum amplitude of the signals by a predetermined factor may be used as the threshold.

By using the group in which the influence of the pipe-supporting-plate protrusions is the greatest as the pipe-supporting-plate-region inspection signal, as described above, the center position of the pipe-supporting plate can be accurately specified without being affected by the deposited scale whose axial position falls outside the pipe-supporting-plate region.

Next, at the evaluation-group selecting section 68, with the same procedure as that in the first embodiment, groups at the gaps are specified, and the sensors belonging to the gap groups are selected as the evaluation sensors.

The evaluation-signal generating section 71 generates signals to be used for estimating the blockage ratios by using signals from the evaluation sensors (measurement points) selected by the evaluation-group selecting section 68. For example, in the case where the blockage ratios are separately estimated for each of the four gaps 26b provided in the through-hole 26, groups are reorganized into collections of sensors for each gap, as in the first embodiment. Specifically, Groups 1 and 2, which are the evaluation groups, are reorganized as follows into Groups A to D for sensors at each gap.

Group A: sensor 1, sensor 2
Group B: sensor 7, sensor 8
Group C: sensor 13, sensor 14
Group D: sensor 19, sensor 20

Next, for each of the reorganized Groups A, B, C, and D, average eddy-current flaw detection signals are determined (see FIG. 13(b)).

Next, as shown in FIG. 13(c), each signal is folded by using the midpoint of the pipe-supporting plate in the heat-conducting-pipe axial direction, determined at the pipe-supporting-plate-center-position specifying section 72, as an axial center, and difference signals between the folded signals and non-folded signals are obtained to be used as evaluation signals (see FIGS. 13(c), (d)). That is, asymmetrical components of the signals across both sides of the center of the pipe-supporting plate are used as the evaluation signals.

Then, as in the first embodiment describe above, the blockage ratios are estimated by using these evaluation signals.

In this way, the following advantages are afforded by the deposit measurement apparatus, the deposit measurement method, and the deposit measurement program according to this embodiment.

Specifically, by utilizing the characteristic that signals originating from the pipe-supporting plate are symmetrical with respect to the thickness-direction center of the pipe-supporting plate, whereas the deposited shapes of the scale are asymmetrical, the midpoint of the axial region of the pipe-supporting plate is set as the pipe-supporting-plate center position; the asymmetrical components are determined by determining the differences in signals across both sides of this center position; and the blockage ratios are estimated by using these asymmetry components. By doing so, errors due to the influence of the pipe-supporting plate can be reduced. As a result, in the case where deposit formation is asymmetrical in the axial direction, the influence on the detected signals due to the pipe-supporting plate can be reduced without having to prepare a special reference signal in advance (for example, an eddy-current flaw detection signal when there is no deposit), and the precision in estimating the blockage ratios can be improved.

In addition, even if the deposit is deposited in a region beyond the midpoint of the axial region of the pipe-supporting plate described above, because the above-described difference-signal amplitudes, which are the asymmetrical components across both sides of the pipe-supporting-plate center position, are correlated with the blockage ratios, the blockage ratios can be estimated with satisfactory precision.

Furthermore, although the method in this embodiment, in which the blockage ratios are estimated by calculating the evaluation characteristic quantities by using the calculated evaluation signals, is the same as that in the first embodiment, a calibration curve or a calculation equation for estimating the blockage ratios is calculated by generating the evaluation signals following the blockage-ratio-estimating method according to the second embodiment.

Note that, to separately estimate the blockage ratio for each of the gaps 26b, the blockage ratio is individually calculated in this embodiment for each of the four Groups A, B, C, and D; however, alternatively, as shown in FIG. 14, difference signals may be obtained by a similar method by using the average eddy-current flaw detection signal of all eddy-current flaw detection signals of the evaluation groups, and the blockage ratios may be estimated by using these difference signals.

For example, with a multi-sensor or a rotating-sensor eddy-current flaw detection probe, when the probe is decentered or tilted in a heat-conducting pipe, the detected signals are influenced by changes in the distance between an inner surface of the heat-conducting pipe and individual coils, the inclination thereof, etc. In other words, in the case where the probe is decentered or tilted, signals acquired by individual sensors differ as compared with the case where the probe is correctly disposed. As described above, however, by taking an average of all eddy-current flaw detection signals in the evaluation groups, and by determining the blockage ratios by using the averaged signal, the influence of decentering of the probe can be reduced, and the precision of estimating the blockage ratios can be further improved.

Note that, although the system of specifying the axial midpoint of the pipe-supporting plate by using grouping has been described herein, the method of specifying the axial midpoint of the pipe-supporting plate is not limited thereto. For example, in the case where the pipe-supporting-plate position can be specified with supplementary sensors, such as ultrasonic test sensors, etc., the axial midpoint of the pipe-supporting plate may be specified by using such sensors.

In the case where the pipe-supporting-plate position can be specified by supplementary means in this way, the measurement points of the eddy-current flaw detection signals to be used for estimating the blockage ratios may be a single point or multiple points in the circumferential direction of the heat-conducting pipe. For example, in the case where the evaluation signal is at a single point in the circumferential direction of the heat-conducting pipe, as in the case of a bobbin-coil sensor, this sensor itself can be selected as the evaluation sensor, the evaluation signal can be generated by a similar processing, and the influence of the pipe-supporting-plate signal having a symmetrical shape in the axial direction can be reduced.

What is claimed is:

1. A deposit measurement apparatus that is applied to a heat exchanger provided with a heat-conducting pipe and a pipe-supporting plate in which a through-hole for inserting the heat-conducting pipe is formed, the through-hole having N protrusions in a circumferential direction of the heat-conducting pipe, and that estimates a blockage ratio of a gap between a wall surface of the through-hole and an outer surface of the heat-conducting pipe or a thickness of a deposit deposited at the gap, the deposit measurement apparatus comprising:

a signal acquisition section for acquiring a flaw detection signal by scanning inside the heat-conducting pipe with a sensor; and a processing section for estimating the blockage ratio at the gap or the thickness of the deposit deposited at the gap by using the flaw detection signal for the gap of the pipe-supporting-plate protrusion in the through-hole;

wherein the signal acquisition section acquires flaw detection signals when M measurement points disposed inside the heat-conducting pipe at equal intervals in the circumferential direction thereof are scanned in the axial direction of the heat-conducting pipe;

wherein the processing section includes an evaluation-group selection section for specifying protrusion groups that can be considered to be positioned at the pipe-supporting-plate protrusions in the through-hole among the flaw detection signals acquired by the signal acquisition section, and for selecting signals from evaluation groups, which are groups other than the protrusion groups, as evaluation sensor signals; and wherein the processing section further includes an estimating section for estimating blockage ratios or thicknesses of deposits by using the evaluation sensor signals.

2. A deposit measurement apparatus according to claim 1, wherein the processing section includes a group-representative-signal calculating section for forming groups so that the flaw detection signals from the measuring points located every M/N measuring points are placed in the same groups and for determining a representative signal for each group; and wherein the evaluation-group selection section specifies the protrusion groups that can be considered to be positioned at the pipe-supporting-plate protrusions in the through-hole on the basis of the representative signals.

3. A deposit measuring apparatus according to claim 2, wherein the evaluation-group selection section uses the number of sensors positioned in an angular range affected by the protrusions as an exclusion number, specifies the same number of representative signals as the exclusion number, and specifies groups to which the specified representative signals belong as the protrusion groups.

4. A deposit measurement apparatus according to claim 2, wherein, of the representative signals, the processing section specifies a midpoint in a pipe-supporting plate region for the representative signals that are judged to be positioned in the angular range affected by the protrusions;

specifies a position in each flaw detection signal of the evaluation groups that is the same as the midpoint; folds each flaw detection signal using the specified position as an axial center; acquires difference signals between folded signals and non-folded signals, thereby determining respective asymmetrical components centered on the midpoints of the flaw detection signals; and estimates blockage ratios or thicknesses of deposits at gaps on the basis of a plurality of the asymmetrical components.

5. A deposit measurement apparatus according to claim 2, wherein, of the representative signals, the processing section specifies a midpoint in a pipe-supporting plate region for the representative signals that are judged to be positioned in the angular range affected by the protrusion;

specifies a position in an evaluation signal obtained from each flaw detection signal of the evaluation groups that is the same as the midpoint; folds each evaluation signal using the specified position as an axial center; acquires difference signals between folded signals and non-folded signals, thereby determining respective asymmetrical components centered on the midpoints of the evaluation signals; and estimates blockage ratios or thicknesses of deposits on at gaps the basis of a plurality of the asymmetrical components.

6. A deposit measurement apparatus according to claim 1, wherein signals acquired by the signal acquisition section are signals acquired by an eddy-current flaw detection system in which a signal factor originating from a magnetic material is added to a correction test piece, and a correction is performed by using a signal obtained with the correction test piece as a reference signal.

7. An eddy-current inspection method of performing detection by employing a deposit measurement apparatus according to claim 1.

8. A deposit measurement apparatus that is applied to a heat exchanger provided with a heat-conducting pipe and a pipe-supporting plate in which a through-hole for inserting the heat-conducting pipe is formed, the through-hole having a substantially symmetrical shape across a plane that passes through a midpoint of the pipe-supporting plate in an axial direction of the heat-conducting pipe and that perpendicularly intersects with the axial direction of the heat-conducting pipe, and that estimates a blockage ratio of a gap between a wall surface of the through-hole and an outer surface of the heat-conducting pipe or a thickness of a deposit deposited at the gap, the deposit measurement apparatus comprising:

a signal acquisition section for acquiring a flaw detection signal by scanning inside the heat-conducting pipe with a sensor; and a processing section for estimating the blockage ratio at the gap or the thickness of the deposit deposited at the gap by using an asymmetrical component of the flaw detection signal across both sides of an axial center position of the pipe-supporting plate;

wherein the signal acquisition section acquires flaw detection signals when M measurement points disposed inside the heat-conducting pipe at equal intervals in the circumferential direction thereof are scanned in the axial direction of the heat-conducting pipe;

wherein the processing section includes an evaluation-group selection section for specifying protrusion groups that can be considered to be positioned at the pipe-supporting-plate protrusions in the through-hole among the flaw detection signals acquired by the signal acquisition section, and for selecting signals from evaluation groups, which are groups other than the protrusion groups, as evaluation sensor signals; and wherein the processing section further includes an estimating section for estimating blockage ratios or thicknesses of deposits by using the evaluation sensor signals.

9. A deposit measurement apparatus according to claim 8, wherein the processing section includes a group-representative-signal calculating section for forming groups so that the flaw detection signals from the measuring points located every M/N measuring points are placed in the same groups and for determining a representative signal for each group; and wherein the evaluation-group selection section specifies the protrusion groups that can be considered to be positioned at the pipe-supporting-plate protrusions in the through-hole on the basis of the representative signals.

10. A deposit measuring apparatus according to claim 9, wherein the evaluation-group selection section uses the number of sensors positioned in an angular range affected by the protrusions as an exclusion number, specifies the same number of representative signals as the exclusion number, and specifies groups to which the specified representative signals belong as the protrusion groups.

11. A deposit measurement apparatus according to claim 9, wherein, of the representative signals, the processing section specifies a midpoint in a pipe-supporting plate region for the representative signals that are judged to be positioned in the angular range affected by the protrusions;

specifies a position in each flaw detection signal of the evaluation groups that is the same as the midpoint; folds each flaw detection signal using the specified position as an axial center; acquires difference signals between folded signals and non-folded signals, thereby determining respective asymmetrical components centered on the midpoints of the flaw detection signals; and estimates blockage ratios or thicknesses of deposits at gaps on the basis of a plurality of the asymmetrical components.

12. A deposit measurement apparatus according to claim 9 wherein, of the representative signals, the processing section specifies a midpoint in a pipe-supporting plate region for the representative signals that are judged to be positioned in the angular range affected by the protrusion;

specifies a position in an evaluation signal obtained from each flaw detection signal of the evaluation groups that is the same as the midpoint; folds each evaluation signal using the specified position as an axial center; acquires difference signals between folded signals and non-folded signals, thereby determining respective asymmetrical components centered on the midpoints of the evaluation signals; and estimates blockage ratios or thicknesses of deposits on at gaps the basis of a plurality of the asymmetrical components.

13. A deposit measurement apparatus according to claim 8, wherein signals acquired by the signal acquisition section are signals acquired by an eddy-current flaw detection system in which a signal factor originating from a magnetic material is added to a correction test piece, and a correction is performed by using a signal obtained with the correction test piece as a reference signal.

14. An eddy-current inspection method of performing detection by employing a deposit measurement apparatus according to claim 8.

15. A deposit measurement method that is applied to a heat exchanger provided with a heat-conducting pipe and a pipe-supporting plate in which a through-hole for inserting the heat-conducting pipe is formed, the through-hole having N protrusions in a circumferential direction of the heat-conducting pipe, and that estimates a blockage ratio of a gap between a wall surface of the through-hole and an outer surface of the heat-conducting pipe or thickness of a deposit deposited at the gap, the deposit measurement method comprising:

a step of acquiring a flaw detection signal by scanning inside the heat-conducting pipe with a sensor; and a step of estimating the blockage ratio at the gap or the thickness of the deposit deposited at the gap by using the flaw detection signal for the gap of the pipe-supporting-plate protrusion in the through-hole;

wherein the step of acquiring includes acquiring flaw detection signals when M measurement points disposed inside the heat-conducting pipe at equal intervals in the circumferential direction thereof are scanned in the axial direction of the heat-conducting pipe;

wherein the step of estimating includes specifying protrusion groups that can be considered to be positioned at the pipe-supporting-plate protrusions in the through-hole among the flaw detection signals acquired by the step of acquiring, and selecting signals from evaluation groups, which are groups other than the protrusion groups, as evaluation sensor signals; and wherein the of estimating further includes estimating blockage ratios or thicknesses of deposits by using the evaluation sensor signals.

16. A deposit measurement method that is applied to a heat exchanger provided with a heat-conducting pipe and a pipe-supporting plate in which a through-hole for inserting the heat-conducting pipe is formed, the through-hole having a substantially symmetrical shape across a plane that passes through a midpoint of the pipe-supporting plate in an axial direction of the heat-conducting pipe and that perpendicularly intersects with the axial direction of the heat-conducting pipe, and that estimates a blockage ratio of a gap between a wall surface of the through-hole and an outer surface of the heat-conducting pipe or a thickness of a deposit deposited at the gap, the deposit measurement method comprising:

a step of acquiring a flaw detection signal by scanning inside the heat-conducting pipe with a sensor; and a step of estimating the blockage ratio at the gap or the thickness of the deposit deposited at the gap by using an asymmetrical component of the flaw detection signal across both sides of an axial center position of the pipe-supporting plate;

wherein the step of acquiring includes acquiring flaw detection signals when M measurement points disposed inside the heat-conducting pipe at equal intervals in the circumferential direction thereof are scanned in the axial direction of the heat-conducting pipe;

wherein the step of estimating includes specifying protrusion groups that can be considered to be positioned at the pipe-supporting-plate protrusions in the through-hole among the flaw detection signals acquired by the step of acquiring, and selecting signals from evaluation groups, which are groups other than the protrusion groups, as evaluation sensor signals; and wherein the step of estimating further includes estimating blockage ratios or thicknesses of deposits by using the evaluation sensor signals.

17. A non-transitory computer-readable storage medium that stores a deposit measurement program that is applied to a heat exchanger provided with a heat-conducting pipe and a pipe-supporting plate in which a through-hole for inserting the heat-conducting pipe is formed, the through-hole having N protrusions in a circumferential direction of the heat-conducting pipe, and that estimates a blockage ratio of a gap between a wall surface of the through-hole and an outer surface of the heat-conducting pipe or a thickness of a deposit deposited at the gap, the non-transitory computer-readable storage medium storing the deposit measurement program for causing a computer to execute:

processing for acquiring a flaw detection signal by scanning inside the heat-conducting pipe with a sensor; and processing for estimating the blockage ratio at the gap or the thickness of the deposit deposited at the gap by using the flaw detection signal for the gap of the pipe-supporting-plate protrusion in the through-hole;

wherein the processing for acquiring includes acquiring flaw detection signals when M measurement points disposed inside the heat-conducting pipe at equal intervals in the circumferential direction thereof are scanned in the axial direction of the heat-conducting pipe;

wherein the processing for estimating includes specifying protrusion groups that can be considered to be positioned at the pipe-supporting-plate protrusions in the through-hole among the flaw detection signals acquired by the processing for acquiring, and selecting signals from evaluation groups, which are groups other than the protrusion groups, as evaluation sensor signals; and wherein the processing for estimating further includes an estimating section for estimating blockage ratios or thicknesses of deposits by using the evaluation sensor signals.

18. A non-transitory computer-readable storage medium that stores a deposit measurement program that is applied to a heat exchanger provided with a heat-conducting pipe and a pipe-supporting plate in which a through-hole for inserting the heat-conducting pipe is formed, the through-hole having a substantially symmetrical shape across a plane that passes through a midpoint of the pipe-supporting plate in an axial direction of the heat-conducting pipe and that perpendicularly intersects with the axial direction of the heat-conducting pipe, and that estimates a blockage ratio of a gap between a wall surface of the through-hole and an outer surface of the heat-conducting pipe or a thickness of a deposit deposited at the gap, the non-transitory computer-readable storage medium storing the deposit measurement program for causing a computer to execute:

processing for acquiring a flaw detection signal by scanning inside the heat-conducting pipe with a sensor; and processing for estimating the blockage ratio at the gap or the thickness of the deposit deposited at the gap by using an asymmetrical component of the flaw detection signal across both sides of an axial center position of the pipe-supporting plate;

wherein the processing for acquiring includes acquiring flaw detection signals when M measurement points disposed inside the heat-conducting pipe at equal intervals in the circumferential direction thereof are scanned in the axial direction of the heat-conducting pipe;

wherein the processing for estimating includes specifying protrusion groups that can be considered to be positioned at the pipe-supporting-plate protrusions in the through-hole among the flaw detection signals acquired by the processing for acquiring, and for selecting signals from evaluation groups, which are groups other than the protrusion groups, as evaluation sensor signals; and wherein the processing for estimating further includes estimating blockage ratios or thicknesses of deposits by using the evaluation sensor signals.

* * * * *